US00PP21777P3

(12) United States Plant Patent
Hancock

(10) Patent No.: US PP21,777 P3
(45) Date of Patent: Mar. 15, 2011

(54) BLUEBERRY PLANT DENOMINATED 'HURON'

(50) Latin Name: *Vaccinium corymbosum*
Varietal Denomination: Huron

(75) Inventor: James F. Hancock, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 12/386,216

(22) Filed: Apr. 15, 2009

(65) Prior Publication Data

US 2010/0269233 P1 Oct. 21, 2010

(51) Int. Cl.
*A01H 5/00* (2006.01)

(52) U.S. Cl. ..... Plt./157

(58) Field of Classification Search ..... Plt./157
See application file for complete search history.

(56) References Cited

U.S. PATENT DOCUMENTS

| | | | |
|---|---|---|---|
| PP15,103 | P3 | 8/2004 | Hancock |
| PP15,146 | P3 | 9/2004 | Hancock |
| PP15,185 | P3 | 9/2004 | Hancock |

*Primary Examiner*—Kent L Bell
(74) *Attorney, Agent, or Firm*—Harness, Dickey & Pierce, P.L.C.

(57) ABSTRACT

'Huron' is a new blueberry cultivar of primarily *Vaccinium corymbosum* from the Michigan State University breeding program. The rest of its parentage is from *V. darrowii* (12.5%) and *V. angustifolium* (3.15%). It is a productive, early ripening cultivar with very high fresh market quality and a long storage life. It is intended for areas where northern highbush cultivars are grown successfully. Plants of 'Huron' are vigorous and upright. Canes are numerous, moderately branched and the fruit are well exposed. Its berries are moderately large, have small, dry picking scars, medium blue color, excellent firmness and superior flavor, if allowed to fully ripen.

2 Drawing Sheets

Latin name and variety denomination: The present invention relates to a new and distinct variety of *Vaccinium corymbosum,* which is hereby denominated 'Huron.'

SUMMARY

The present invention relates to a new and distinct variety of highbush blueberry plant, denominated 'Huron.' 'Huron' is a new blueberry cultivar of primarily *Vaccinium corymbosum* from the Michigan State University breeding program. The rest of its parentage is from *V. darrowii* (12.5%) and *V. angustifolium* (3.15%). It is a productive, early ripening cultivar with very high fresh market quality and a long storage life. It is intended for areas where northern highbush cultivars are grown successfully. Plants of 'Huron' are vigorous and upright. Canes are numerous, moderately branched and the fruit are well exposed. Its berries are moderately large, have small, dry picking scars, medium blue color, excellent firmness and superior flavor, if allowed to fully ripen. The size of the fruit is unusually regular and is presented in a loose cluster.

BRIEF DESCRIPTION OF THE DRAWINGS

The present invention will become more fully understood from the detailed description and the accompanying drawings, wherein.

DETAILED BOTANICAL DESCRIPTION

Figure 1:
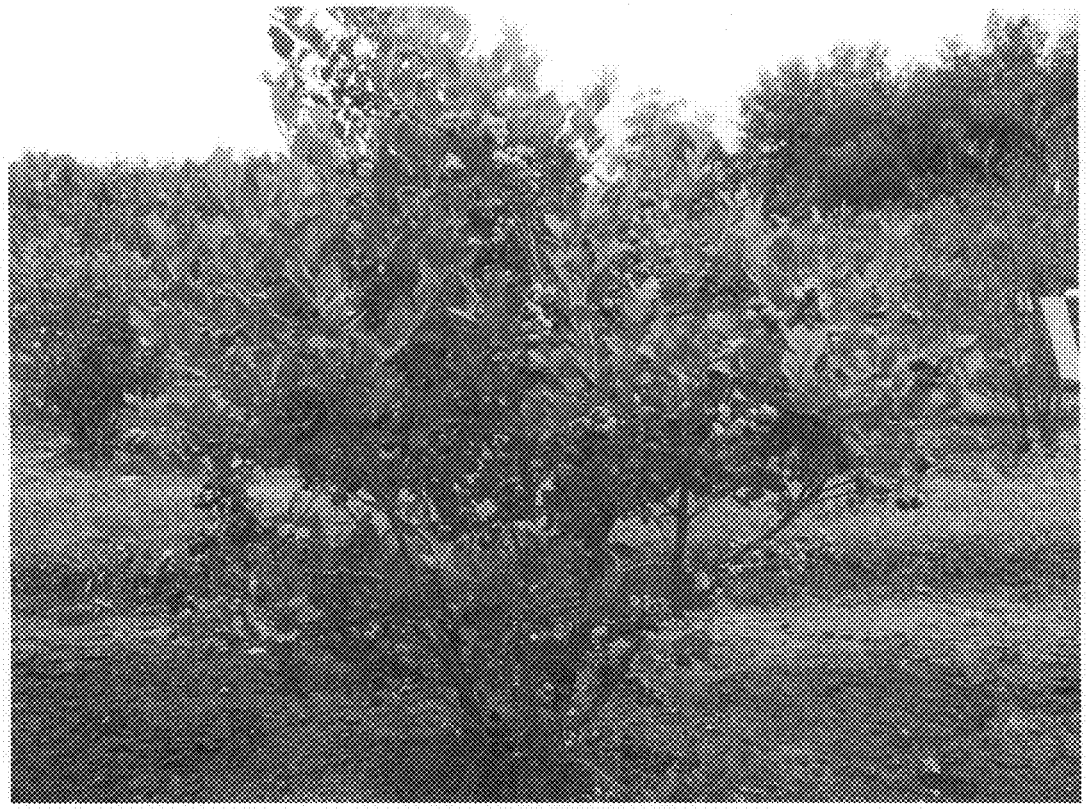
FIG. 1 is a photographic print in full color of a 'Huron' blueberry bush in the late stage of ripening, where the bush is in the foreground and the additional plants or portions thereof in the background and the grass on the ground are not part of the 'Huron' blueberry plant.
Figure 2:
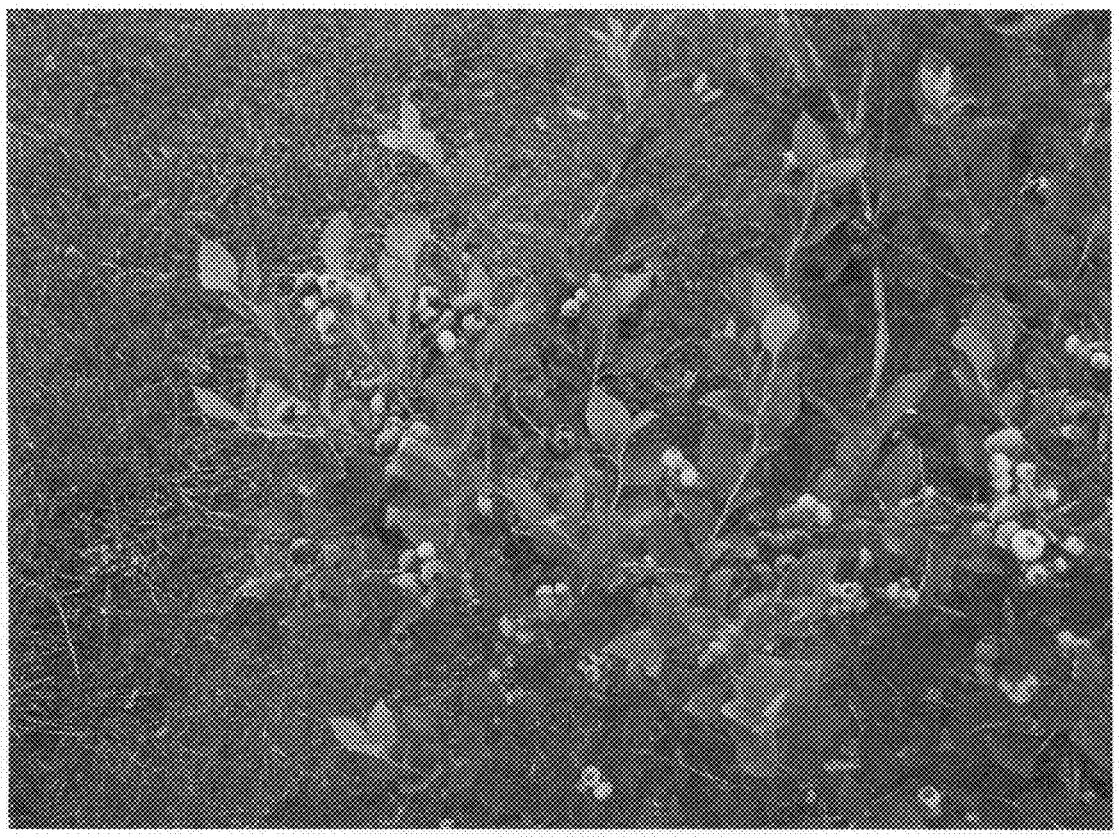
FIG. 2 is a photographic print in full color illustrating a 'Huron' branch with exemplary fruit clusters, where most, but not all, of the fruit shown is mature.

The following is a detailed botanical description of the new and distinct variety of blueberry denominated 'Huron,' its flowers, fruit and foliage. The original selection of 'Huron' was evaluated at the Southwest Michigan Research and Extension at Benton Harbor, Mich. for ten years. Hardwood cuttings were also set in a replicated design with 26 other Michigan State University selections at Grand Junction, Mich., South Haven, Mich., Lacota, Mich., Corvallis, Oreg., and Lowell, Oreg. The plantings in Michigan were evaluated for seven years, while the plantings in Oregon were evaluated for two years.

The first harvest of 'Huron' falls between the most widely grown early cultivar 'Duke' and the most important midseason ones, 'Draper' and 'Bluecrop'. 'Huron' has larger fruit than 'Bluecrop' and 'Duke', as well as a longer shelf life. It is a little smaller fruited than 'Draper' with slightly darker fruit, but its fruiting season is earlier. 'Draper' is described in "Blueberry plant denominated 'Draper,'" U.S. Plant Pat. No. 15,103 to Hancock, which was filed on Jan. 23, 2003 and issued Aug. 24, 2004, the disclosure of which is incorporated herein by reference.

Emasculated flowers of MU-6566, the male parent (i.e., the seed parent), were pollinated in 1991 with pollen from G-344U, the female parent. The seeds were germinated, grown in a greenhouse for 1 year and then field planted at the Southwest Michigan Research and Extension Center (SWMREC) in Benton Harbor, Mich. 'Huron' was selected from a group of 87 siblings in 1997.

MU-6566 [MU-22 ('Ashworth'×'Bluecrop')×MU-13 ('Ashworth'×'Earliblue')] originated from the USDA/ARS collaborative breeding program. It was originally selected at Jonesboro, Me. and evaluated later at Grand Junction, Mich. for 6 years. It had an unusually late flowering date for an early genotype and very high yields, but its fruit were dark and weak flavored. G-344 [US 75 ('Bluecrop'×*V. darrowii* Fla 4b)×Elizabeth)], also came from the USDA/ARS collaborative breeding program and was originally selected in Hammonton, N.J. It was later evaluated at Grand Junction, Mich. for 10 years. The fruit of G-344 were firm, powder blue with a pleasant, complex flavor, but many of its flower buds were damaged by winter cold, presumably due to a high contribution (25%) of the native southern species, *V. darrowii,* in its ancestry.

'Huron' is moderately self-fertile but requires' pollination from another highbush blueberry cultivar for maximum fruit development.

'Huron' may be propagated by hardwood cuttings in a greenhouse and then planted in the field. Initiation of root development from hardwood cuttings may take about four to six weeks. In addition, 'Huron' may be propagated by rooted softwood cuttings. Furthermore, generation of micro-shoots in a greenhouse using established tissue culture methods may be used to produce plants of 'Huron.'

Initiation of root development from microshoots takes about three to four weeks. Such methods are discussed in the following references: Doran, W. L. and Bailey, J. S. "Propagation of the high bush blueberry by softwood cuttings," Bulletin Massachusetts Agricultural Experiment Station; no. 410. Amherst, Mass. Massachusetts State College, 1943; Doehlert, C. A. "Propagating blueberries from hardwood cuttings," Circular (New Jersey Agricultural Experiment Station) 490. New Brunswick, N.J. New Jersey Agricultural Experiment Station, 1945; Doehlert, C. A. "Propagating blueberries from hardwood cuttings," Circular (New Jersey Agricultural Experiment Station) 551. New Brunswick, N.J.: New Jersey Agricultural Experiment Station, 1953; Zimmerman, R. H. 1991. Micropropagation of temperate zone fruit and nut crops. In: Debergh, P. C. and Zimmerman, R. H. (eds.) Micropropagation: Technology and application. Kluwer, Dordreckt; El Shiekh, A.; Wildung, D. K.; Luby, J. J.; Sargent, K. L.; Read, P. E. "Long term effects of propagation by tissue culture or softwood single node cuttings on growth habit, yield, and berry weight of 'Northblue' blueberry," Journal of the American Society for Horticultural Science. 1996, 121: 2, 339 342; Galletta, G. J.; Ballington, J. R.; Daubeny, H. A.; Brennan, R. M.; Reisch, B. J.; Pratt, C.; Ferguson, A. R.; Seal, A. G.; McNeilage, M. A.; Fraser, L. G.; Harvey, C. F.; Beatson, R. A.; Hancock, J. F.; Scott, D. H.; Lawrence, F. J.; Janick, J. (ed.); Moore, J. N. "Fruit breeding. Volume II. Vine and small fruits," Department of Horticulture, Purdue University, West Lafayette, Ind. 1996 John Wiley and Sons; New York; USA; Strik, B.; Brun, C.; Ahmedullah, M.; Antonelli, A.; Askham, L.; Barney, D.; Bristow, P.; Fisher, G.; Hart, J.; Havens, D. Draper A. D. and Chandler C. K. "Accelerating highbush blueberry selection evaluation by early propagation," Journal of the American Society for Horticultural Science. 1986 111(2): 301-303; Pritts M. P. and Hancock J. F. (Eds.) "Highbush blueberry production guide," Northeast Regional Agricultural Engineering Service, Ithaca, N.Y., USA 1992.

Taxonomic characteristics disclosed herein are standard in the practice (R E Gough, R J Hindle, and V G Shutak, "Identification of Ten Highbush Blueberry Cultivars using Morphological Characteristics," *HortScience* 11 (5): 512-4, 1976). Color descriptions, except those given in common terms, are presented in Royal Horticultural Society Colour Chart designations. In cases where the color descriptions cited from The Royal Horticultural Society Colour Chart differ from the colors shown in the drawings, the colors cited from The Royal Horticultural Society Colour Chart should be considered accurate. Any deviation from these colors in the drawings is due to failure of the photographic process to exactly duplicate the colors of nature. In addition, fruit color designations in Table 1 are applicable only to mature fruit.

TABLE 1

'Huron' Characteristics

| Characteristic | 'Huron' |
|---|---|
| Bush: | |
| Mature height: | 1.4 m |
| Mature width: | 0.9 m |
| Height/width ratio: | 1.5 |
| Growth habit: | Upright |
| Annual renewal canes: | 32-65 |
| Internode length on spring shoots: | 2-3 cm |
| Mature cane color: | Grayed-green (197A) |
| Mature cane length: | 1.0-1.4 m |
| Mature cane width: | 0.5-2.5 cm |
| Bark texture: | Smooth to rough |
| Fall color on new shoots: | Yellow green (146C) with blushes of red-purple (61B) |
| Foliage: | |
| Leaf shape: | Ovoid to Elliptic |
| Apex shape: | Acute |
| Base shape: | Obtuse |
| Leaf length: | 4.7-6.7 cm (5.4 cm average) |
| Leaf width: | 2.0-2.8 cm (2.6 cm average) |
| Leaf length/width ratio: | 2.0 |
| Leaf margin: | entire |
| Leaf nectarines: | Absent |
| Pubescence: | none |
| Color upper surface: | green (137C) |
| Color lower surface: | green (138C) |
| Petiole length: | 3.0 cm |
| Petiole color: | Green (137C) |
| Bud: | |
| Bud shape: | Oblanceolate |
| Bud width: | 2.0-3.0 mm (2.1 mm average) |
| Bud length: | 4.1 mm-5.3 mm (5.1 mm average) |
| Color: | Reddish-brown |
| Blossoms: | |
| Shape of corolla: | Elongate-ureolate |
| Calyx: | 5 lobed |
| Style length: | 7-9 mm |
| Color of open flower: | White |
| Flower # per cluster: | 8-9 |
| Pistil: | One per flower |
| Pistil Color: | Green (137A) |
| Pistil length: | 7-9 mm |
| Flower diameter: | 5-6 mm |
| Flower length: | 7-9 mm |
| Fragrance: | Faint blueberry aroma |
| Reproductive Organs: | |
| Type: | Berry |
| Seed size: | 1.7 mm |
| Number of seeds: | 20-50 (42 average) |
| Mature fruit: | |
| Length: | 1.0-1.2 cm (1.1 cm average) |
| Width: | 1.5-1.9 cm (1.75 cm average) |
| Color: | Violet Blue (98A) |

TABLE 1-continued

| 'Huron' Characteristics | |
|---|---|
| Characteristic | 'Huron' |
| Shape: | Globose, uniform |
| Color with bloom: | Violet blue (98D) |
| Color without bloom: | Blue (103A) |
| Pedicel scar size: | 1.8 mm |
| Pedicel length: | 4-6 mm |
| Pedicel color: | Green (137A) |
| Peduncle length: | 5-6 cm |
| Peduncle color: | Green (137A) |
| Average weight: | 1.7 g |

Consistent high yields at multiple sites in Michigan indicate that the buds and wood of 'Huron' are tolerant to fluctuating late fall and spring temperatures. It is exceptionally late flowering and was one of the few early to mid-season genotypes to survive a late frost in the mid-1990s. 'Huron' also has excellent winter hardiness, as it has routinely been challenged with mid-winter temperatures below −20° C.

In the trials conducted in Michigan at Grand Junction, 'Huron' was consistently one of the top rated advanced selections. It had among the highest fruit load of any of the early to midseason cultivars and the best flavor, as illustrated in Tables 2, 3, and 5. The average date of first harvest was 5 days before 'Draper' and six days after 'Duke'. The fruit of 'Huron' was slightly softer than 'Draper' and much firmer than 'Bluecrop' and 'Duke'. 'Huron's' fruit were smaller than 'Draper', but larger than 'Duke' and 'Bluecrop'. Its fruit color was similar to 'Duke', but a little darker than 'Bluecrop' and 'Draper'. 'Huron' fruit had a storage life as long as 'Draper', which was several weeks longer than 'Duke' and 'Bluecrop,' as illustrated in Table 4. 'Huron' had the second highest levels of soluble solids next to 'Draper' and the second lowest acidity next to 'Duke'. The evaluations done at Lacota and South Haven were informal, but generally mirrored the observations made at Grand Junction.

In the trials conducted in Oregon, 'Huron' was superior to all but a few of the advanced selections. However, its yields were not as high as in Michigan and its fruit were a little softer and smaller. Its fruit flavor and firmness was superior to 'Bluecrop,' but not 'Draper.' 'Draper' and 'Bluecrop' also had higher yields than 'Huron'.

TABLE 2

Mean fruit ratings and ranges (parenthesis) of 'Duke,' 'Huron,' 'Draper,' and 'Bluecrop' at Grand Junction, Michigan from 2001-2007. Two year old plants were set in 1999 at 4 × 10' spacing with 26 other Michigan State University selections. Evaluations were made when the bushes were about 50% ripe.

| Cultivar | Date of 1st harvest | Weight (g) | Color | Picking scar | Firmness | Flavor | Fruit load |
|---|---|---|---|---|---|---|---|
| 'Duke' | 7/3 (6/26-7/11) | 1.5 (1.4-2.0) | 7[Z] (7-8) | 8 (7-9) | 8 (7-9) | 6 (5-7) | 7 (7-9) |
| 'Huron' | 7/9 (6/28-7/22) | 1.7 (1.6-1.9) | 7 (7-8) | 8 (7-9) | 8 (7-9) | 9 (8-9) | 8 (8-9) |
| 'Draper' | 7/14 (7/10-7/19) | 2.1 (1.5-2.6) | 8 (8-9) | 9 (8-9) | 9 (8-9) | 8 (8-9) | 8 (7-9) |

TABLE 2-continued

Mean fruit ratings and ranges (parenthesis) of 'Duke,' 'Huron,' 'Draper,' and 'Bluecrop' at Grand Junction, Michigan from 2001-2007. Two year old plants were set in 1999 at 4 × 10' spacing with 26 other Michigan State University selections. Evaluations were made when the bushes were about 50% ripe.

| Cultivar | Date of 1st harvest | Weight (g) | Color | Picking scar | Firmness | Flavor | Fruit load |
|---|---|---|---|---|---|---|---|
| 'Bluecrop' | 7/14 (7/4-7/21) | 1.6 (1.4-2.0) | 8 (7-8) | 7 (7-8) | 7 (7-8) | 6 (5-7) | 7 (8-9) |

[Z]The rating scale 1-9, with 1-4 = inferior, 5-6 = acceptable, 7 = good, 8 = very good, and 9 = superior.

TABLE 3

Taste panel results for 'Duke ,' 'Huron,' 'Draper,' and 'Bluecrop' in 2006 and 2007. The taste panel consisted of 25-30 individuals representing a cross section of the East Lansing, MI community. The panelists were given 5 fully ripe fruit of each variety and were ask to sample the fruit together. They rated it from 1 (poor) to 10 (superior) for sweetness, tartness, texture and overall flavor.

| Cultivar | Sweetness | Tartness | Texture | Overall Flavor |
|---|---|---|---|---|
| 'Duke' | 5.1 (5.1-5.2) | 6.0 (6.0-6.3) | 7.2 (7.1-6.9) | 5.9 (5.6-6.2) |
| 'Huron' | 6.2 (5.8-6.6) | 5.7 (5.6-5.8) | 6.9 (6.5-7.3) | 7.2 (7.0-7.4) |
| 'Draper' | 5.3 (4.7-6.0) | 6.1 (5.7-6.5) | 7.5 (7.5-7.6) | 6.6 (6.1-7.0) |
| 'Bluecrop' | 6.1 (5.7-6.5) | 6.0 (5.8-6.2) | 7.0 (6.9-7.1) | 7.2 (7.1-7.3) |

TABLE 4

Chemical and physical measurements of the fruit of 'Duke', 'Huron', 'Draper,' and Bluecrop' harvested in Grand Junction Michigan in 2006 and 2007. Five fruit samples were evaluated for soluble solids (SS), titratable acidity (TA) and firmness (g/mm). Storage life was calculated as the number of weeks that the majority of fruit remained firm at 5° C.

| Cultivar | SS | TA | SS/TA | Firmness (g/mm) | Storage life |
|---|---|---|---|---|---|
| 'Duke' | 11.6 (10.8-12.4) | 0.59 (0.58-0.61) | 19.7 (17.7-21.3) | 302 (250-352) | 3.0 (1.0-5) |
| 'Huron' | 11.5 (11.0-12.0) | 0.65 (0.61-0.69) | 17.7 (18.0-17.4) | 359 (336-383) | 6.0 (5-7) |
| 'Draper' | 12.9 (12.9-13.0) | 0.81 (0.97-0.65) | 15.9 (13.2-20.0) | 345 (320-365) | 6.0 (5-7) |
| 'Bluecrop' | 11.0 (10.0-12.0) | 0.82 (0.75-0.89) | 13.4 (13.3-13.5) | 202 (180-222) | 2.5 (1-4) |

TABLE 5

Mean fruit ratings of 'Draper,' 'Huron,' and 'Bluecrop' at Lowell and Corvallis, OR from 2001-2002. Two-year-old plants were set in 2000 at 4 × 10' spacing with 26 other Michigan State University selections. Evaluations were made when the bushes were 50% ripe. All values were similar in the two years.

| Location | Cultivar | Fruit load | Size | Color | Picking scar | Firmness | Flavor |
|---|---|---|---|---|---|---|---|
| Corvallis | 'Draper' | 8[Z] | 8 | 8 | 8 | 9 | 8 |
| | 'Huron' | 7 | 7 | 7 | 7 | 8 | 8 |
| | 'Bluecrop' | 8 | 7 | 7 | 7 | 7 | 6 |

TABLE 5-continued

Mean fruit ratings of 'Draper,' 'Huron,' and 'Bluecrop' at Lowell and Corvallis, OR from 2001-2002. Two-year-old plants were set in 2000 at 4 × 10' spacing with 26 other Michigan State University selections. Evaluations were made when the bushes were 50% ripe. All values were similar in the two years.

| Location | Cultivar | Fruit load | Size | Color | Picking scar | Firm-ness | Flavor |
|---|---|---|---|---|---|---|---|
| Lowell | 'Draper' | 8 | 8 | 8 | 8 | 9 | 8 |
| | 'Huron' | 7 | 7 | 7 | 7 | 8 | 7 |
| | 'Bluecrop' | 8 | 7 | 7 | 7 | 7 | 6 |

[Z]The rating scale 1-9, with 1-4 = inferior, 5-6 = acceptable, 7 = good, 8 = very good, and 9 = superior.

Blueberry growers in Michigan and the cooler production regions across the USA, Europe, and Canada will find 'Huron' desirable as a new early northern highbush variety. However, some fruit pedicles of 'Huron' fruit remain attached in very hot weather. The fruit of 'Huron' also develops sugar slowly and if picked too early can be very tart. In addition, the fruit clusters of 'Huron' are relatively tight, which may reduce picking efficiency.

What is claimed is:

1. A new and distinct highbush blueberry plant, substantially as illustrated and described herein.

* * * * *